(12) United States Patent
Kals (10) Patent No.: US 9,320,887 B2
(45) Date of Patent: Apr. 26, 2016

(54) OBJECTIVE ALLOCATION OF IMPLANT ELECTRODE BANDS BASED ON EXCITATION SPREAD

(71) Applicant: MED-EL Elektromedizinische Geraete GmbH, Innsbruck (AT)

(72) Inventor: Mathias Kals, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/516,693

(22) Filed: Oct. 17, 2014

(65) Prior Publication Data

US 2015/0112408 A1    Apr. 23, 2015

Related U.S. Application Data

(60) Provisional application No. 61/891,930, filed on Oct. 17, 2013.

(51) Int. Cl.
| | |
|---|---|
| *A61F 11/04* | (2006.01) |
| *A61F 11/00* | (2006.01) |
| *A61N 1/36* | (2006.01) |
| *A61N 1/05* | (2006.01) |
| *A61N 1/08* | (2006.01) |

(52) U.S. Cl.
CPC ............... *A61N 1/0541* (2013.01); *A61N 1/08* (2013.01); *A61N 1/36032* (2013.01); *A61N 2001/083* (2013.01)

(58) Field of Classification Search
USPC ........................................................ 607/57
See application file for complete search history.

(56) References Cited

U.S. PATENT DOCUMENTS

| | | | |
|---|---|---|---|
| 5,626,629 | A | 5/1997 | Faltys et al. |
| 2007/0179565 | A1 | 8/2007 | Overstreet et al. |
| 2009/0125081 | A1 | 5/2009 | Spitzer et al. |
| 2009/0125082 | A1 | 5/2009 | Schleich |
| 2011/0230934 | A1 | 9/2011 | Zierhofer |
| 2012/0065705 | A1 | 3/2012 | Kals |

OTHER PUBLICATIONS

International Searching Authority, Authorized Officer Blaine R. Copenheaver, International Search Report and Written Opinion—PCT/US2014/061032, date of mailing Mar. 24, 2015, 16 pages.

*Primary Examiner* — Carl H Layno
*Assistant Examiner* — Jon Eric C Morales
(74) *Attorney, Agent, or Firm* — Sunstein Kann Murphy & Timbers LLP (57) ABSTRACT

A cochlear implant arrangement is described for creating sound perception in an implanted patient. An implant electrode contains electrode wires for carrying stimulation signals to corresponding electrode contacts distributed along a length of an outer surface of an apical electrode array section of the implant electrode. An apical portion of the electrode array is characterized by a tendency to fold back against a more basal section of the electrode array when inserted into a cochlea of the patient. An implantable stimulation processor produces the stimulation signals such that each electrode contact, including any in a folded back portion, delivers stimulation signals for a frequency band defined based on a function of spatial spread of stimulation voltage and correctly associated with tonotopic frequency response of the adjacent neural tissue.

18 Claims, 10 Drawing Sheets

OBJECTIVE ALLOCATION OF IMPLANT ELECTRODE BANDS BASED ON EXCITATION SPREAD

This application claims priority from U.S. Provisional Patent Application 61/891,930, filed Oct. 17, 2013, which is incorporated herein by reference in its entirety.

FIELD OF THE INVENTION

The present invention relates to coding stimulation pulses for cochlear implant systems.

BACKGROUND ART

Figure 1:
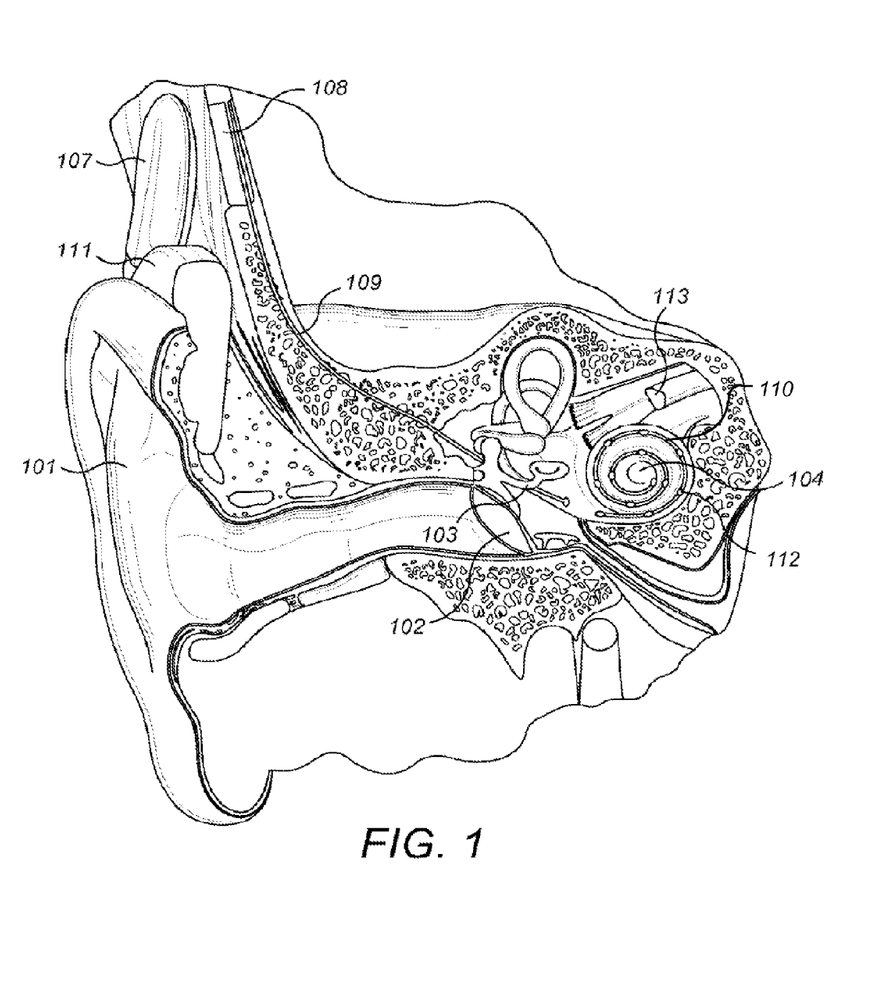
FIG. 1 shows anatomical structures in a human ear having a cochlear implant system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission via coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Along the elongate axis of the electrode array 110 on its surface are multiple electrode contacts 112 that provide selective stimulation of the cochlea 104 e.g., by either monophasic or bi-phasic stimulation. The spacing between the electrode contacts 112 can be constant or variable. For example the electrode contacts 112 at the basal end of the electrode array 110 (closer to where the array enters the cochlea, e.g., through the oval window) may be more widely separated than those at the apical end of the electrode array 110.

Most existing cochlear implant stimulation coding strategies represent a sound signal by splitting it into distinct frequency bands and extracting the envelope (i.e., energy) of each of these bands. These envelope representations of the acoustic signal are used to define the pulse amplitude of stimulation pulses to each electrode. The number of band pass signals typically equals the number of stimulation electrodes, and relatively broad frequency bands are needed to cover the acoustic frequency range. Each electrode contact delivers electric stimulation signals to its adjacent neural tissue for a defined frequency band reflecting the tonotopic organization of the cochlea.

One neglected aspect in cochlear implant (CI) fittings is optimization of the frequency-band allocation of each electrode channel since the determination of place pitch using a psychoacoustic procedure is very time consuming. Generally, the perceived pitch is strongly correlated to the location of neural excitation along the cochlea (tonotopy). In normal hearing, the frequency-place map is logarithmic as defined by Greenwood (Greenwood, 1961). When several electrode channels excite similar regions of neuronal structures, more or less equal perceived pitch can be expected. If these electrode channels present different frequency-band signals to the same neurons, spectral- and temporal-confusion can result.

During electrode implantation surgery, the surgeon advances the electrode array through the oval window into the basal end of the scala tympani of the cochlea such that the distal tip of the electrode array reaches the apical region of the cochlea. But the high flexibility of the electrode array means that the surgical insertion procedure bears a significant risk of "fold-overs" of the electrode array within the cochlea. Particularly the apical tip of the electrode array may fold-over and the electrode contacts within the folded apical end will not reach the apical region of the cochlea, but instead will stimulate a more basal region of the cochlear which will elicit pitch confused hearing impressions in the implanted patient.

Such electrode fold-overs can be detected by imaging methods, e.g. computer tomographic scan (Grolman at al., "Spread of Excitation Measurements for the Detection of Electrode Array Foldovers: A Prospective Study Comparing 3-Dimensional Rotational X-ray and Intraoperative Spread of Excitation Measurements", 2008). Such a complex and costly procedure is necessary because other measures such as eCAPs do not allow for distinguishing between a region where the neuronal nerve does not respond and situations where an electrode fold-over occurred; the measurement results do not allow any criteria to be established to differentiate between the two cases.

SUMMARY OF THE INVENTION

Embodiments of the present invention are directed to detecting a location of a fold-over in an implanted cochlear implant electrode. For each electrode contact in an implanted electrode array eCAP measurements are performed. Then current spread is calculated for each electrode contact as a function of the eCAP measurements. Based on the current spread calculations, a location of a fold-over in the electrode array is determined where an apical portion of the electrode array has folded back against a more basal section of the electrode array.

In further specific embodiments, neural excitation spatial spread voltage measurements may be performed for each electrode contact, and then the current spread can be calculated a function of the eCAP measurements and the spatial spread voltage measurements. Or impedance field telemetry (IFT) measurements may be performed for each electrode contact, and then the current spread can be calculated as a function of the eCAP measurements and the IFT measurements. Calculating the current spread for each electrode contact also may use a limited number of electrode contacts on each side of the electrode contact being measured.

Embodiments of the present invention also include a novel cochlear implant arrangement for creating sound perception in an implanted patient. An implant electrode contains electrode wires for carrying stimulation signals to corresponding electrode contacts distributed along a length of an outer surface of an apical electrode array section of the implant electrode. An apical portion of the electrode array is characterized by a tendency to fold back against a more basal section of the electrode array when inserted into a cochlea of the patient. An implantable stimulation processor produces the stimulation signals such that each electrode contact, including any in a folded back portion, delivers stimulation signals for a frequency band defined based on a function of spatial spread of stimulation voltage and correctly associated with tonotopic frequency response of the adjacent neural tissue.

The function of spatial current spread may be further based on an amplitude growth function and/or an exponential function. The function of spatial current spread may be based on impedance field telemetry (IFT) measurements. The function of spatial current spread may be defined using a spatial spread matrix.

DETAILED DESCRIPTION OF SPECIFIC EMBODIMENTS

Embodiments of the present invention are directed to using current spread at the electrode contacts to detect fold-over of the electrode array and subsequent adaptation during stimulation. Once a fold-over is detected, a mapping can be made of the electrode contacts to the various frequency channels and from this an optimal frequency band allocation to each electrode contact. The current spread can be calculated in various ways such as by neural excitation spatial spread (SS) voltage measurements and eCAP (electrically-evoked compound action potentials) threshold measurements or by Impedance Field Telemetry (IFT). One specific embodiment detects electrode array fold-over starting with performing eCAP measurements and determining the amplitude growth function and the eCAP threshold. In spatial current spread SS measurements, a constant stimulus current is used for each electrode contact. This allows an estimation of current spread based on measured SS voltages where for any missing values (no eCAP detectable), an interpolation can be used to achieve a complete dataset.

The electrode contacts j of an electrode array having N electrode contacts are numbered from 1 of the apical most electrode contact of the electrode array to N of the basal most electrode contact of the electrode array. The eCAP voltage is the measured peak-to-peak voltage difference of the eCAP response signal between N1 and P1 (Seyle, K. and Brown, C. J., "Speech perception using maps based on neural response telemetry measures", Ear Hear 23 (1 Suppl.), pages 72S-79S, 2002). It is understood that other eCAP response peak-to-peak signals may be used in the same manner, for example N1 and P2 or any combination thereof. To a first approximation a typical peak-to-peak eCAP voltage $U_{P1\_N1}$ is linearly related to stimulation current I (a growth function) when a specific threshold eCAPthr is crossed. Below this stimulation current no eCAP response is measurable and $U_{P1\_N1}=0$. An idealized linear growth function can be described as shown in FIG. 2 by:

$$U_{P1\_N1} = \max(d \times (I - eCAPthr), 0) \quad \text{(Eq. 1)}$$

Figure 2:
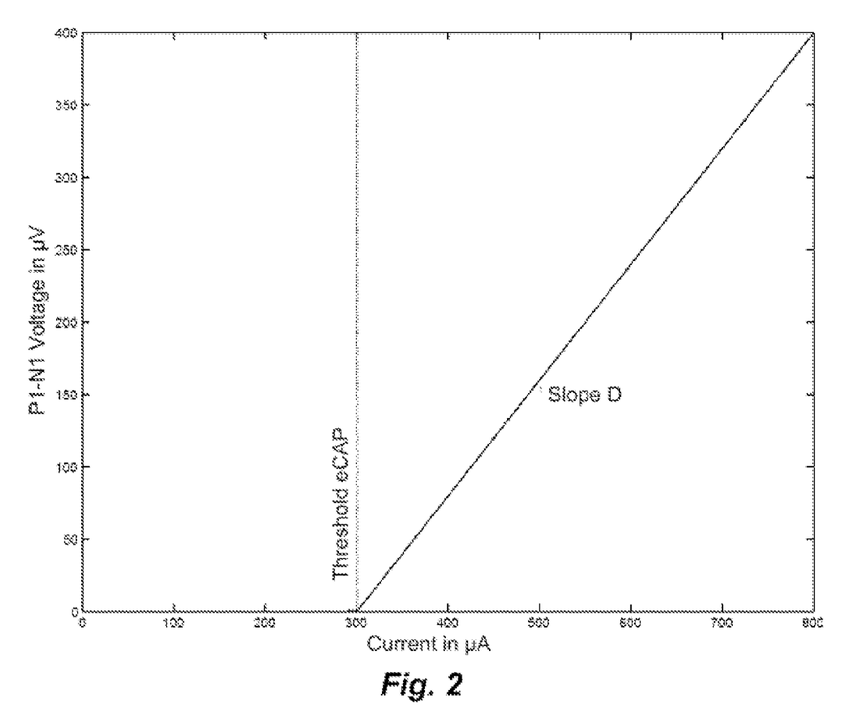
FIG. 2 shows a graph of idealized eCAP growth function was a function of stimulation current.

In the measurements shown in FIG. 2, the eCAPthr is 300 μA and slope d=0.8 V/μA. The slope d and threshold eCAPthr depends on neuronal survival and geometric properties such as location and distance between neurons and electrode contacts, and consequently vary from electrode contact to electrode contact. Alternatively, other models besides a linear amplitude growth may similarly work, e.g. an exponential model:

$$U_{P1\_N1} = f(I, eCAPthr)$$

Figure 3:
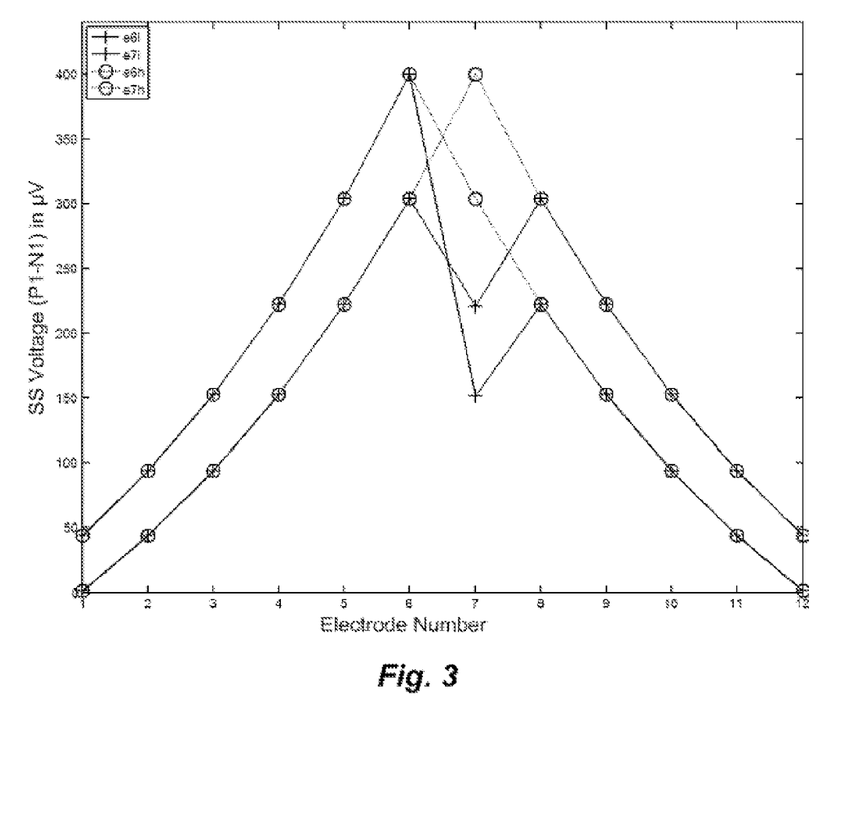
FIG. 3 shows a graph of spatial spread voltages from one set of experiments.

In SS voltage profiles across electrode contacts, starting from the stimulation electrode contact a monotonic falling function can be expected on a straight cochlea with an optimal positioning of the electrode array without fold-overs and assuming a homogeneous neuronal survival (no "dead" regions). This can be seen in curves e6h and e7h of FIG. 3. In regions with lower neuronal survival ("dead" regions), the neural response is decreased and leads to sinks or reduced values in SS voltage profiles as shown in curves e6i and e7i of FIG. 3. The presence of an electrode fold-over is indicated by a sink and an additional peak beside the stimulation electrode in a SS profile (Grolman et al., 2008). Such a sink may be present in cases of both dead regions and fold-overs, and without any additional information (e.g. X-ray image or CT-scan), it is not possible to distinguish between the two different cases.

To overcome this problem and since current spread is relatively unaffected by neuronal survival, the corresponding current spread can be calculated based on measured SS voltages and eCAPthr. For this, eCAP thresholds eCAPthr$_i$ are determined for each electrode contact i and a SS matrix $SS_{i,j}$ with row index i for stimulated electrode contact and column index j for measured electrode contact. A stimulation current $I_0$ is determined such that max(eCAPthr$_i$)<$I_0$≤min(MCL$_i$) for all electrode contacts i of the electrode array. Any missing values can be interpolated using a spline or any other appropriate target function for complete eCAPthr$_i$ and $SS_{i,j}$ datasets. A relation of the spatial spread voltage matrix $SS_{i,j}$ and current spread matrix $I_{i,j}$ gives a normalized SS matrix SSnorm$_{i,j}$:

$$SSnorm_{i,j} = \frac{SS_{i,j}}{SS_{j,j}} = \frac{I_{i,j} - eCAPthr_j}{I_0 - eCAPthr_j} \quad \text{(Eq. 2)}$$

Assuming equal stimulation currents $I_0$ for each electrode contact is an acceptable simplification which is not dependent on a given amplitude growth function. In general it would be possible to use different specific stimulation currents $I_{0i}$ for each electrode contact instead of a common current $I_0$. This may be particularly important when $MCL_i$ and $eCAPthr_i$ currents across the electrode array do not allow using a common $I_0$ current as stated above. In that case, $SS_{normi,j}$ is calculated with the same Equation 2, but replacing the stimulation current $I_0$ common to all electrode contacts i, with the electrode contact specific stimulation current $I_{0i}$.

The stimulation current $I_0$, or in case of electrode contact specific stimulation current $I_{0i}$, is then applied to one electrode contact and the voltage $U_{P1-N1}$ is measured on the other electrode contacts. This measurement may be repeated several times and the voltage $U_{P1-N1}$ may be estimated from these measurements. The measurement is further repeated for each electrode contact i of the electrode array.

Because no measurement for the stimulated electrode contact i can be obtained, $SS_{j,j}$ is calculated from the model of the amplitude growth function with the applied stimulation current $I_0$ or in case of electrode contact specific stimulation current $I_{0i}$. Any scaling factors in the model for the amplitude growth function cancel out. In case of the linear model, this is slope $d_j$.

The current spread $I_{i,j}$ with i the stimulated electrode contact and j the measured electrode contact can be calculated from the measured SS voltages, and taking the amplitude growth function into account, as follows:

$$I_{i,j} = \frac{SS_{i,j}}{SS_{j,j}} \times (I_0 - eCAPthr_j) + eCAPthr_j \quad \text{(Eq. 3)}$$

The difference $D_{ik}$ is calculated as $I_{i,k+1} - I_{i,k}$ if k<I, or else $I_{i,k} - I_{i,k+1}$ if k≥i. Here i denotes the electrode contact that has been stimulated and k an index running from 1 to N−1, where N is the number of electrode contacts the electrode array has. Note that this is not just a derivative.

An estimation of the current spread $I_{i,j}$ can also be made by Impedance Field Telemetry (IFT) measurements. In that case, stimulation artifacts on active electrodes and common ground electrode need to be considered in the measured voltage matrix $U_{i,j}$. Based on this voltage matrix and the channel impedances $Z_j$ the current spread matrix can be calculated by $$I_{i,j} = \frac{U_{i,j}}{z_j} \quad \text{(Eq. 4)}$$

Figure 4:
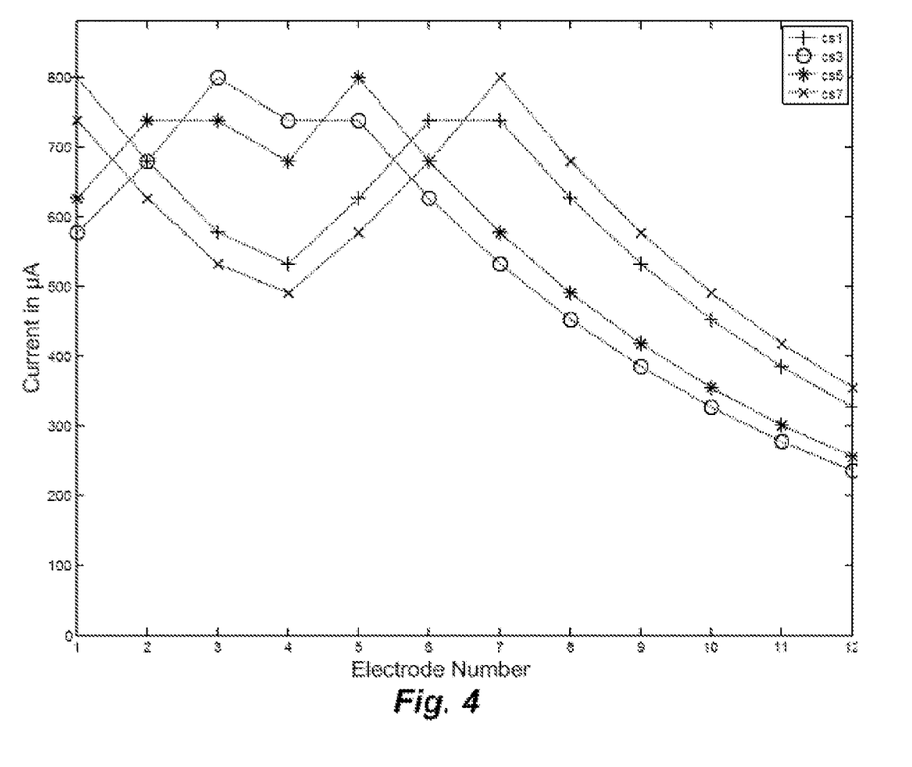
FIG. 4 shows a graph of current spreads when a foldover is simulated between electrode contacts 3 and 4.
Figure 5:
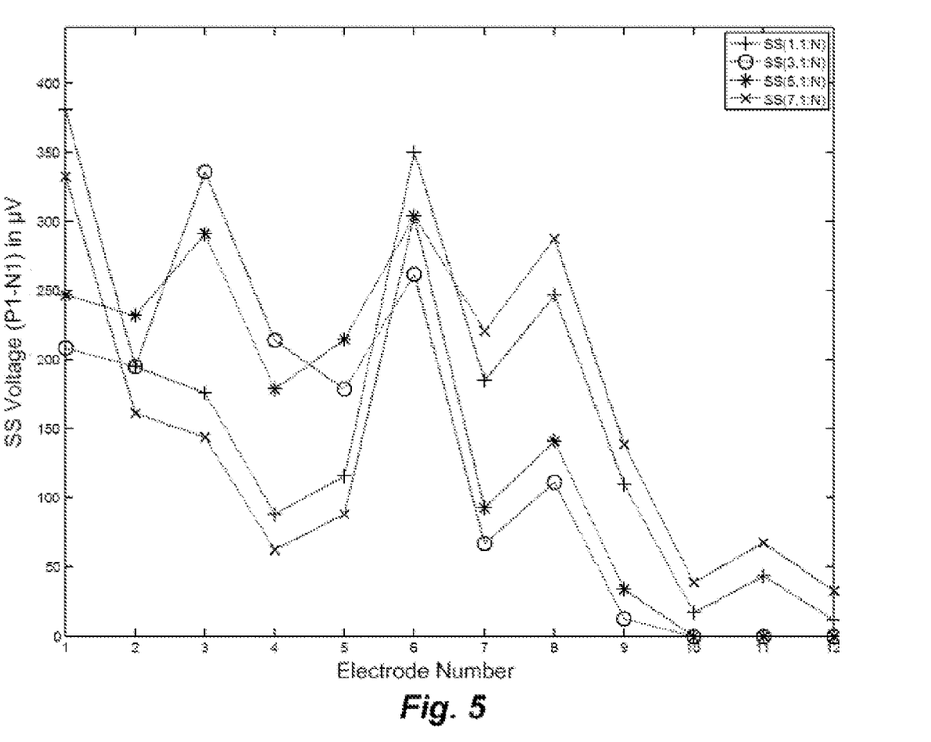
FIG. 5 shows a graph of spatial spread voltages from the current spreads of FIG. 4.
Figure 6:
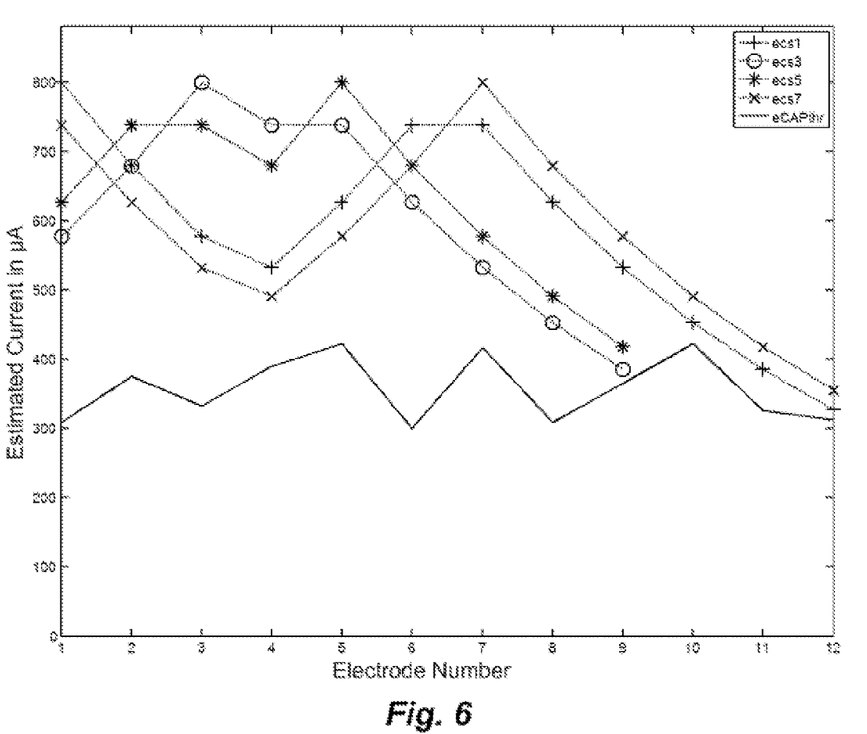
FIG. 6 shows a graph of estimated current spreads determined from the spatial spreads of FIG. 5.

In FIGS. 4 and 5, $I_{i,j}$ and $SS_{i,j}$ datasets are shown for when electrode contacts 1, 3, 5 or 7 is stimulated at 800 μA and an electrode fold-over is located between electrode contacts 3 and 4. This is simulated by a position vector x=[6.5 5.5 4.5 4 5 6 7 8 9 10 11 12] and thresholds eCAPthr=300e−6*[0.97 0.80 0.90 0.77 0.71 1.00 0.72 0.97 0.82 0.71 0.92 0.96]. In FIG. 5, the $SS_{7,j}$ spread of electrode contact 7 has, for example, several turn-points at electrode contacts 4, 7 and 10. Based on Equation 3, the underlying current spread $I_{7,j}$ can be estimated where only one turn-point is present at electrode contacts 4 in ecs7 as shown in FIG. 6. This leads to easy detection of electrode fold-over where estimated $I_{i,j}$ currents are used and scanned for local maximum beside the global maximum (position of stimulation electrode contact i) since an additional local maximum can indicate a fold-over.

Figure 9:
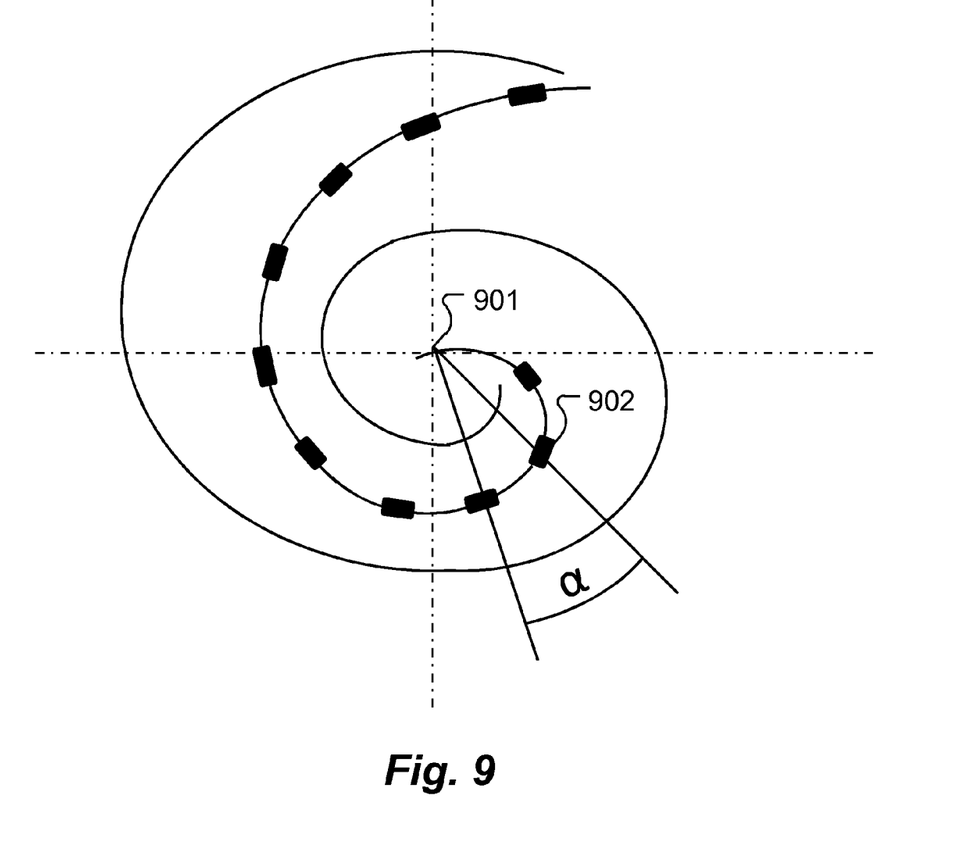
FIG. 9 illustrates the idea of electrode contact angle in an electrode array inserted into a patient cochlea.

In order to avoid turn-crosstalk, only a limited number of electrode contacts may be considered for evaluation, i.e. not more than some given number of neighboring electrode contacts away from the stimulated electrode contact. This number of electrode contacts is referred to as the window-size and extends symmetrically on both sides from the stimulated electrode contact. This may reflect an electrode contact separation angle α as shown in FIG. 9 that characterizes the angular separation between electrode contacts 902 (with respect to an angular vertex located at the central cochlear axis 901). Depending on the specific patient physiology, different contact separation angles α may be suitable including position dependent angles. For example the most apical electrode contacts may be separated by a larger angle and the more basal electrode contacts may be separated by a smaller angle. Any function that maps the angle dependency on electrode contact position is suitable as well. Typically the contact separation angle α between electrode contacts 902 may average around 55°. To avoid turn-crosstalk a maximal angle between the left-most and right-most electrode contact 902 may for example be constrained not exceed 270°. With an electrode array having an electrode contact spacing typically around 2 mm, a windows-size of 9 may be determined. The actual specific window-size may vary depending on the electrode array that is used, the maximal contact separation angle α between left-most and right-most electrode contacts 902, and the size of the cochlea so that determining the contact separation angle α between adjacent electrode contacts 902 and may vary from patient to patient.

Figure 7:
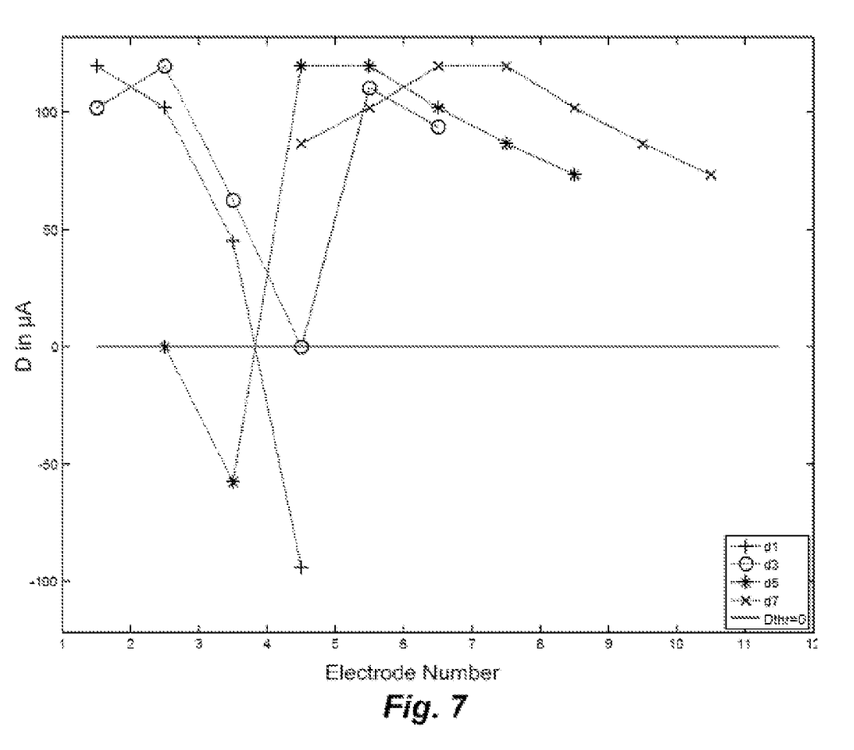
FIG. 7 shows a graph of differences in current between adjacent electrodes with a foldover between electrode contacts 3 and 4.

FIG. 7 shows difference values between adjacent electrode contacts where, for example, curve d1 shows the data for when electrode contact 1 was stimulated. Thus the d1 curve corresponds to $D_{1,k}$ for any k that fits into the window-size. For any k outside the window-size, the d1 line will be cut off and set to zero. Once the d1 function is derived, the detection of the fold-over starts from basal most electrode contact and advancing to the more apical contact searching for the first zero-crossing which indicates the presence of an electrode fold-over. If there is no such zero-crossing, then no fold-over is present. In FIG. 7, there is a zero crossing on curve d5 between electrode contacts 3 and 4 indicating the presence of an electrode fold-over there between.

Based on the fold-over detection results, a new electrode-contact to frequency-band allocation may be performed. For frequency band allocation the percept of electrical stimulation is of interest, therefore normalized spatial-spread voltage matrix $SSnorm_{i,j}$ is used in the following.

Figure 10:
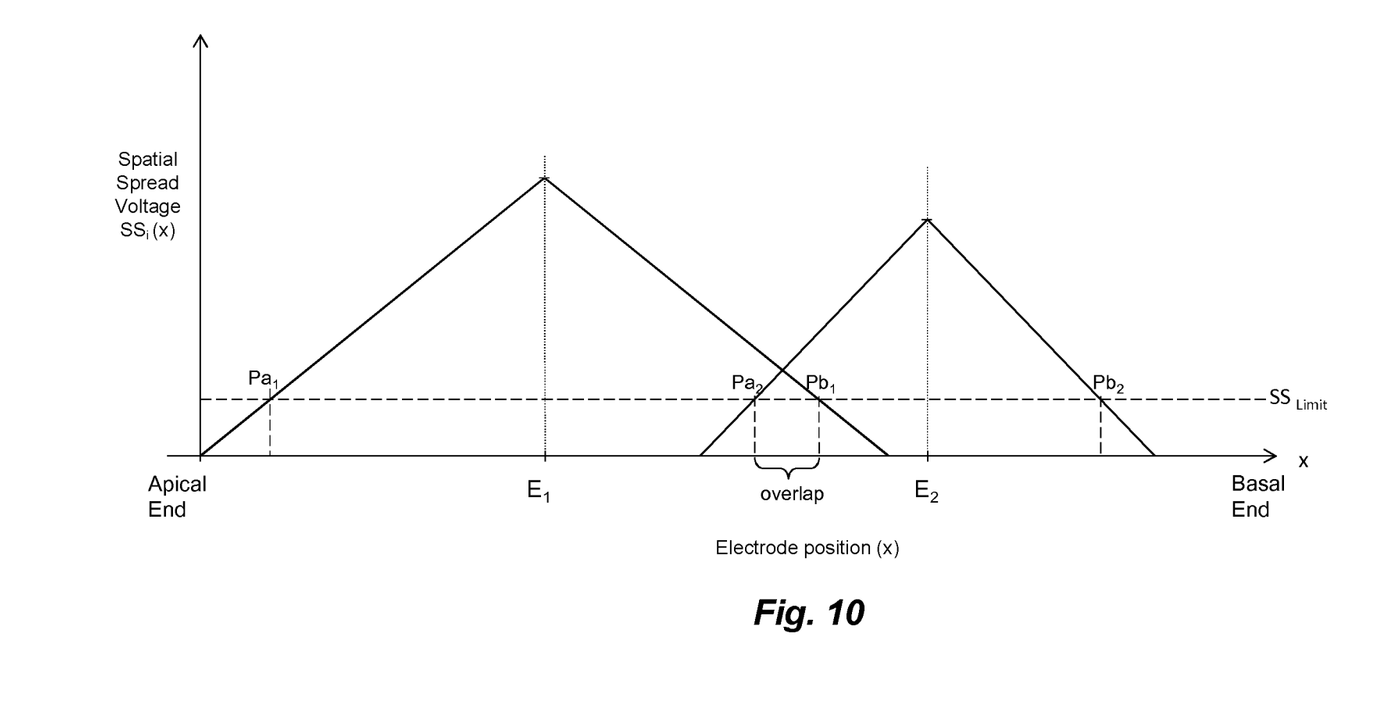
FIG. 10 shows an example of spatial spread voltage function overlap data.

In one specific example, spatial spread along the measured electrode contact dimension j may be expressed as a function of electrode contact position on the electrode array, turning the spatial-spread voltage matrix $SS_{i,j}$ into a set of functions $SS_{i(x)}$ where i is the stimulated electrode contact and x the position on the electrode array in a one-dimensional space. The functions $SS_{i(x)}$ may be normalized and the window-size translates to a length on the electrode array. As illustrated in FIG. 10, starting from a position of the stimulated electrode contact i, denoted by $x_i$, an apical direction limit to the spatial spread voltage function $Pa_i$ is determined by the electrode position x where the function $SS_{i(x)}$ reaches or drops below a certain limit $SS_{limit}$ or where the position of the window-size is reached. In the same manner in a basal direction limit is denoted by $Pb_i$. The basal and apical direction limits may be different and furthermore may depend on the position and/or the electrode contact i. The limit may be obtained from statistical properties of the measured spatial-spread measures $SS_{i,j}$ and/or properties of the desired filter bank.

In another specific example, the normalized spatial-spread voltage matrix $SSnorm_{i,j}$ is up-sampled for each stimulated electrode contact along the measured electrode contact dimension j. This means, that for the stimulated electrode contact i any measured values between electrode contacts j are interpolated. Any suitable interpolation, e.g. linear or spline, can be used. These interpolated or up sampled values can be denoted by $SSint_{i,f}$ where f is the up sampling index introducing M points between adjacent electrode contacts: f={1,1+1/M, 1+2/M, . . . , 1+(M−1)/M, 2, . . . , N}. In one example the up sampling may be expressed by:

$$SSdB_{i,f} = 20 \times \log 10\left(\frac{SS_{int_{i,j}}}{\max(SS_{int_{i,f}})}\right) \quad \text{(Eq. 5)}$$

The values $Pa_i$ and $Pb_i$ are determined in the same manner as above, but for example the limit may be expressed in dB and for example be −3 dB. Note that if $SS_{jj}$=max($SS_{jj}$) (which is not necessarily always true), then SSnorm is already normalized and so SSint already includes the normalization and division by max($SSint_{i,f}$) which should correspond with $SS_i$, $i*M$ where M is the up sampling factor and be already 1. The normalization according the long-term average speech spectra (Byrne et. Al., 1994) can be done additionally by adding long term dB values relative to spectral maximum within the range of lower and upper frequency bank limits (e.g., according to Greenwood frequency-to-place function), or the long term average speech spectra can also be utilized in the spatial spread matrix limit SSlimit.

Having determined $Pa_i$ and $Pb_i$ for all electrode contacts N of the electrode array, a next step is determining an overlap index Oindex, indicating the percentage of overlap between adjacent electrode contacts in terms of spatial spread (channel interaction) by:

$$Oindex_i = \begin{cases} \frac{Pb_i - Pa_{i+1}}{Pb_i - Pa_i}, & \text{if } i = 1 \\ \frac{(Pb_i - Pa_{i+1}) + (Pb_{i-1} - Pa_i)}{Pb_i - Pa_i}, & \text{if } 1 < i < N \\ \frac{Pb_{i-1} - Pa_i}{Pb_i - Pa_i}, & \text{if } i = N \end{cases} \quad \text{(Eq. 6)}$$

See FIG. 10. Then electrode contacts i are compared to a limit Olimit and those electrode contacts are excluded whose $Oindex_i$ equals or exceeds Olimit. Olimit may be a fixed value for all electrode contacts, or it may be electrode contact specific, for example, as a function of the electrode contact position x on the electrode array.

The electrode contacts then may be re-indexed in case one electrode contact is excluded. This may be done, for example, By comparing the electrode contacts i starting from basal-most electrode contact with Olimit (which take into account the position of the electrode contact), or it may be done after determining all the electrode contacts to be excluded. Such re-assigned electrode contact indexes are denoted by e in the following and may include no new indexing, i.e. e=i. For example, Olimit may be determined by $$O_{limit} = \text{median}(O_{index_i}) \times (1 + O_{prop}) + O_{Offset} \quad \text{(Eq. 7)}$$

where median($Oindex_i$) is the median value over all electrode contacts N of the electrode array and Ooffset and Oprop are individual constants (e.g., both may equal zero). In case of negative values of $O_{limit}$, a fold-over detection and re-mapping may be performed as described herein.

The lower $Pl_e$ and higher $Ph_e$ cut-off positions for the remaining electrode contacts e on the electrode array then are calculated. For example this includes calculating:

$$Pl_e = \begin{cases} 2P_e - \frac{Pb_e + Pa_{e+1}}{2}, & \text{if } e = 1 \\ \frac{Pb_{e-1} + Pa_e}{2}, & \text{if } 1 < e \le N \end{cases} \quad \text{(Eq. 8)}$$

and $$Ph_e = \begin{cases} \frac{Pb_e + Pa_{e+1}}{2}, & \text{if } 1 \le e < N \\ 2P_e - \frac{Pb_{e-1} + Pa_e}{2}, & \text{if } e = N \end{cases}$$

The location of the electrode contact e is represented by $P_e$. For electrode e=1 and e=N a symmetric band-width is calculated. Instead of using a symmetric band-width within first and last electrode an average band-width can be calculated by:

$$Pl_1 = P_1 - \frac{1}{N-1}\sum_{e=2}^{N} P_e - Pa_e \text{ and} \quad \text{(Eq. 9)}$$

$$Ph_N = P_N + \frac{1}{N-1}\sum_{e=1}^{N-1} Pb_e - P_e$$

Finally the frequency bands for each electrode contact e can be calculated from the lower $Pl_e$ and higher $Ph_e$ cut-off positions with the help of the Greenwood-function as a mapping function:

$$F = A \times (10^{ax} - k), \quad \text{(Eq. 10)}$$

with A, a and k constants chosen based on gender or other physiologic empirical values. For example, for an adult male, typical values may be A=165.4 and a=2.1 and k=0.88. The constant a is chosen such that x expresses the proportion of basilar length. Or the mapping can be estimated by known empiric values. The lowest frequency covered by the basal most electrode contact on position $Pa_1$ on the electrode array typically is $F_1$=100 Hz, and the highest frequency covered by the apical most electrode contact on position $Pb_N$ on the electrode array typically is $F_2$=8500 Hz. Inserting both into the Greenwood-function, $x_1$ corresponding to the apical-most position of the frequency in relation to the cochlea and $x_2$ corresponding to the basal-most position of the frequency in relation to the cochlea can be calculated. From this the position on the electrode array can be mapped to the frequency region f in the cochlea with:

$$F = A \times (10^{ax} - k), \text{ and} \quad \text{(Eq. 11)}$$

$$x = \frac{(p \times (x_1 - x_2) + x_2 \times Pa_1 - x_1 \times Pb_N)}{Pa_1 - Pb_N}$$

Figure 8:
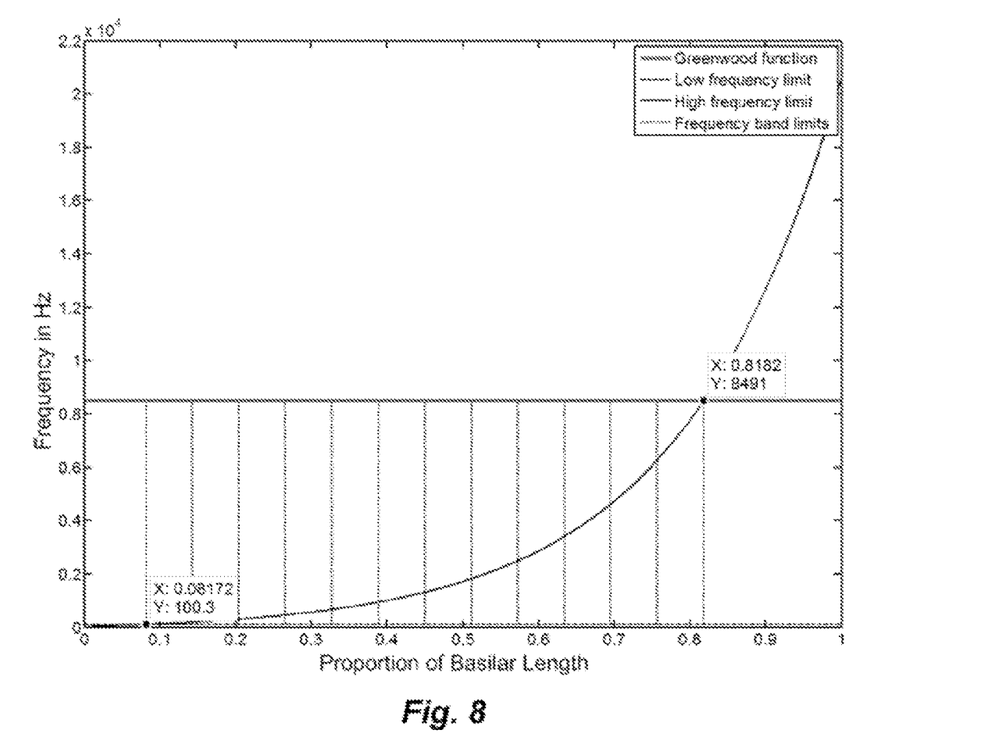
FIG. 8 shows a graph of electrode contact frequency allocation based on Greenwood function.

The result of this for one set of experiments is shown in FIG. 8 where the frequency limits $F_1$ and $F_2$ above are used and a symmetric spread around electrode contact e with a width of $Pb_e - Pa_e$=1 is assumed. The frequency-band limits are indicated at the crossing point of Greenwood function and band limits.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for detecting a location of a fold-over in an implanted cochlear implant electrode, the method comprising:
    performing eCAP measurements and neural excitation spatial spread voltage measurements for each electrode contact in an implanted electrode array;
    calculating current spread for each electrode contact as a function of the eCAP measurements and the spatial spread voltage measurements; and
    based on the current spread calculations determining a location of a fold-over in the electrode array where an apical portion of the electrode array has folded back against a more basal section of the electrode array.

2. The method according to claim 1, further comprising:
    performing impedance field telemetry (IFT) measurements for each electrode contact, and wherein calculating the current spread is a function of the eCAP measurements, the spatial spread voltage measurements, and the IFT measurements.

3. The method according to claim 1, wherein calculating the current spread for each electrode contact uses a limited number of electrode contacts on each side of the electrode contact being measured.

4. A cochlear implant electrode measurement arrangement comprising:
    means for performing eCAP measurements for each electrode contact in an implanted electrode array;
    means for performing neural excitation spatial spread voltage measurements for each electrode contact;
    means for calculating current spread for each electrode contact as a function of the eCAP measurements and the spatial spread voltage measurements; and
    means for determining a location of a fold-over in the electrode array based on the current spread calculations where an apical portion of the electrode array has folded back against a more basal section of the electrode array.

5. The measurement arrangement according to claim 4, further comprising:
    means for performing impedance field telemetry (IFT) measurements for each electrode contact, and wherein calculating the current spread is a function of the eCAP measurements, the spatial spread voltage measurements, and the IFT measurements.

6. The measurement arrangement according to claim 4, wherein the means for calculating the current spread for each electrode contact uses a limited number of electrode contacts on each side of the electrode contact being measured.

7. A method for creating sound perception, the method comprising:
    using a function of spatial current spread defined using a spatial spread matrix to determine tonotopic frequency response of neural tissue adjacent to each of a plurality of electrode contacts distributed along a length of an outer surface of an apical electrode array section of an implant electrode inserted into a cochlea of the patient; and
    based on the determined frequency response producing stimulation signals in a frequency band defined for each electrode contact for perception by the patient as sound.

8. The method according to claim 7, wherein at least one of the electrode contacts is located in an apical portion of the electrode array that is folded back against a more basal section of the electrode array.

9. The method according to claim 7, wherein the function of spatial current spread is based on eCAP threshold measurements.

10. The method according to claim 9, wherein the function of spatial current spread is further based on an amplitude growth function.

11. The method according to claim 9, wherein the function of spatial current spread is further based on an exponential function.

12. The method according to claim 7, wherein the function of spatial current spread is based on impedance field telemetry (IFT) measurements.

13. A cochlear implant arrangement comprising:
    an implant electrode containing a plurality of electrode wires for carrying stimulation signals to a corresponding plurality of electrode contacts distributed along a length of an outer surface of an apical electrode array section of the implant electrode; and
    an implantable stimulation processor coupled to the electrode wires for producing the stimulation signals such that each electrode contact including any in a folded back portion delivers stimulation signals for a frequency band defined based on a function of spatial current spread defined using a spatial spread matrix and correctly associated with an ordered tonotopic frequency response of the adjacent neural tissue.

14. The arrangement according to claim 13, wherein an apical portion of the electrode array is characterized by a tendency to fold back against a more basal section of the electrode array when inserted into a cochlea of the patient.

15. The arrangement according to claim 13, wherein the function of spatial current spread is based on eCAP threshold measurements.

16. The arrangement according to claim 15, wherein the function of spatial current spread is further based on an amplitude growth function.

17. The arrangement according to claim 15, wherein the function of spatial current spread is further based on an exponential function.

18. The arrangement according to claim 13, wherein the function of spatial current spread is based on impedance field telemetry (IFT) measurements.

* * * * *